United States Patent
Ortega et al.

(10) Patent No.: US 6,585,377 B2
(45) Date of Patent: Jul. 1, 2003

(54) DEVICE AND METHOD THAT ALLOWS AN OBJECTIVE MEASUREMENT TO BE TAKEN OF THE SIZE AND MORPHOLOGICAL PATTERN OF THE DEGRADATION OF THE IMAGE IN SCOTOPIC VISION

(75) Inventors: Angel Ramón Gutiérrez Ortega, Murcia (ES); Miguel Ortega Tomás, Valencia (ES); Salvador Santos Pacheco, Murcia (ES); Emilio Sanz Amorós, Valencia (ES); Félix Santatecla Carro, Alicante (ES); Vicente Castelló Picó, Almassera (ES); José Rubira Fernández, Murcia (ES); Santiago Fombuena Gómez, Lliria (ES); Emilio Villaseca Buitrago, Murcia (ES); Javier Mares Antón, Valencia (ES); Jose Luis Rodriguez Rodriguez, Barcelona (ES); Jaime Miralles del Imperial Mora, Murcia (ES)

(73) Assignee: Novosalud, S.L., Valencia (ES)

(*) Notice: Subject to any disclaimer, the term of this patent is extended or adjusted under 35 U.S.C. 154(b) by 102 days.

(21) Appl. No.: 09/875,813

(22) Filed: Jun. 5, 2001

(65) Prior Publication Data

US 2002/0044259 A1 Apr. 18, 2002

(51) Int. Cl.⁷ .................................................. A61B 3/02
(52) U.S. Cl. ....................................................... 351/243
(58) Field of Search ................................ 351/222, 223, 351/237, 239, 240, 241, 242, 243, 246

(56) References Cited

U.S. PATENT DOCUMENTS 4,239,351 A * 12/1980 Williams et al. ............ 351/243
4,550,990 A * 11/1985 Trispel et al. ............... 351/243

OTHER PUBLICATIONS

"A Subjective Method for the Measurement of Monochromatic Aberrations of the Eye", H.C. Howland et al., J. Opt. Soc. Am., vol. 67, No. 11, Nov., 1977.
"Corneal Light Scattering and Visual Performance in Myopic Individuals With Spectacles, Contact Lenses, or Excimer Laser Photorefractive Keratectomy", Chris P. Lohmann, M.D., et al., American Journal of Ophthalmology, 115:444–453, Apr., 1993.

(List continued on next page.)

Primary Examiner—George Manuel
(74) Attorney, Agent, or Firm—Brinks Hofer Gilson & Lione

(57) ABSTRACT

Device and method that allows an objective measure to be taken of the size and morphological pattern of the degradation of the image in scotopic vision. It consists of a black front screen (1) which has a central luminous source (2) surrounded by a grid of circular light spots (3) which at the beginning of the test light up sequentially or at random, according to the method selected, from the nearest to the central source of glare in a centrifuge fashion to the outermost, and a trigger which the patient will press every time he can discriminate the presence of each of the spots in 12 meridians. The non-discriminated or hidden spots will border an area which is interpreted as being occupied by the light aberration and is used as a basis for calculating the glare index.

22 Claims, 1 Drawing Sheet

OTHER PUBLICATIONS

"Corneal Light Scattering After Excimer Laser Photorefractive Keratectomy: The Objective Measurements of Haze", Chris P. Lohmann, M.D., et al., Refractive & Corneal Surgery, vol. 8, Mar./Apr., 1992.

"Laboratory Evaluation of a Clinical Glare Tester", David Miller, M.D., et al., Arch Ophthal–vol. 87, Mar., 1972.

"Glare Sensitivity and Visual Acuity After Excimer Laser Photorefractive Keratectomy for Myopia", Ulrike Niesen et al., British Journal of Ophthalmology, 1997: 81: 136–140.

"Corneal Optical Aberrations Induced by Photorefractive Keratectomy", Katherine M. Oliver et al., Journal of Refractive Surgery, vol. 13, May/Jun., 1997.

"Ocular Optical Aberrations After Photorefractive Keratectomy for Myopia and Myopic Astigmatism", Theo Seiler, M.D. et al., ARCH Ophthalmol/vol. 118, Jan. 2000.

* cited by examiner

DEVICE AND METHOD THAT ALLOWS AN OBJECTIVE MEASUREMENT TO BE TAKEN OF THE SIZE AND MORPHOLOGICAL PATTERN OF THE DEGRADATION OF THE IMAGE IN SCOTOPIC VISION

This invention is a device and method that allows an objective measurement to be taken of the size and morphological pattern of the degradation of the image in scotopic vision, thanks to which it is possible to correct phenomena of glare and scotopic vision of light sources. It is a direct method of evaluation of these alterations or aberrations.

ANTECEDENTS OF THE INVENTION

Nowadays, the development and improvement of refractive surgery techniques and their posterior widespread diffusion have increased interest among ophthalmologists in the control of visual quality.

The complaints of some patients concerning phenomena of glare and scotopic vision of light sources, with the prototypical or most common case being that caused by the headlights of oncoming vehicles while driving at night, have encouraged for some time now the need to know more about these sources and the introduction of different methods for their evaluation.

Glare tests have been used in the widest variety of illnesses such as keratoconus, corneal oedema, cataract and capsular opacification, as well as in the evaluation of the optic quality of intraocular lenses and refractive surgery.

The very complexity of the psychophysical perception of these phenomena of glare, the nature of the factors that cause them, as well as the wide variety of associated pathologies, make it difficult to evaluate them objectively using a standardized test method.

The typical manifestation is the appearance of aberrations in night vision of light sources, such as the headlights of an oncoming vehicle.

In general, any alteration of the parts of the eye that disperse light or multinodal patterns of focal distribution has the potential to produce aberrations of this type.

Previous studies on the results of refractive surgery with excimer laser consider that the component of dispersion of intracorneal light in the "beam" is the main pathogenic factor of "starbust". In these patients, as is the case with other conditions which involve loss of transparency in the eyes, the reduction in contrast of the retinal image could be determined by the quantity of light dispersed.

Most of the tests available for the evaluation of this phenomenon study the effect of a glaring light source on contrast sensitivity tests or low contrast visual acuity optotypes.

Furthermore, the corneal dioptre power differential, between the treated and untreated area, is indicated as being responsible for the halo. Consequently, decentring and the small diameters of the ablated area, as well as the characteristics of the transition zone and the amplitude of pupillary excursions, are factors that favour this phenomenon. This focal multinodal distribution could also be responsible for the appearance of aberrations of scotopic vision of light sources both in patients who wear intraocular lenses, cataract post-surgery (in this case, obviously, the dioptre power differential would refer to the areas occupied and not occupied by the intraocular lens in the pupil), and in irregular processes on the cornea. To date, most authors evaluate these alterations using questionnaires or other subjective interpretations, and no sufficiently contrasted method of quantitative evaluation exists which has shown itself to have the high reproductive capacity of this phenomenon.

Although it is true that the previously mentioned methods of exploration are interesting and evaluate an important aspect of visual function, the correlation established between the results of these tests and the complaints of the patients is still being questioned. Moreover, considering the very fact that the perception of the distortion of night vision of light sources is responsible for discomfort and not the capacity to discriminate details or contrasts, it is considered necessary to introduce a new approach in the study of these visual anomalies.

Measurement of visual acuity or contrast using glare devices (BAT Mentor, Miller-Nadler glare test) shows that it is obvious that they provide an indirect evaluation of visual function which, although interesting, does not describe the halo or starbust which in fact leads to the complaint of those affected.

DESCRIPTION OF THE INVENTION

This device and method which allows an objective measurement to be taken of the size and morphological pattern of the degradation of image in scotopic vision consists of a front screen, with a completely dark background and which includes a central light source surrounded by a series of circular light spots laid out in a radial fashion.

The central light source that will be used as a reference for fixing has a diameter of 10 millimeters and luminance that varies according to the calibration carried out via software.

The grid which covers the central light source is composed of circular spots which are one millimeter in diameter and have the same light intensity as that selected for the central light source, laid out in 12 meridian lines. They are spaced according to the optimal configured progression, in which the first concentric circle of spots closest to the centre maintains a distance of 4 millimeters from the centre; the second, third and fourth concentric circles maintain a distance of 5 millimeters from the previous one, whereas from the fifth to the tenth the distance extends to 10 millimeters between each one.

The device described incorporates a remote control trigger, with a button, which, when pressed, produces a memorization of the target light spot. The spot is lit up and retained in memory for later processing. The device is in turn equipped with a port/connection that, via software, makes possible the compilation of this type of data, which, after processing by a computer, is printed, in the form of a map or area used for the calculation of the glare index.

Analytical test method of image degradation in scotopic vision

The light intensity of the spots is calibrated according to the patient and type of test to be carried out. The system is based on the control of a spot 1 mm in diameter around a central spot 10 mm in diameter. This spot circulates over the sectors in different modes of functioning according to their definition by the user from the software control:

mode 1: sequential, covering all the spots of the dial.
mode 2: sequential, covering only the part with greatest point intensity (closest to the central spot)
mode 3: random, covering all the spots of the dial.
mode 4: random, covering only the part with greatest point intensity (closest to the central spot)
mode 5: mode defined by the user, who selects the spots which he/she wants to be illuminated, these will go sequentially around the central spot.

With the interior in darkness and the patient at two meters from the test device, the patient is encouraged to fix one eye on the central light source, with the other eye covered until the end of the test.

If the process selected is sequential, the test begins with illumination of the spots of the test grid from the nearest to the central source of glare in centrifuge fashion towards the outermost, in the first and successive meridians.

If the process selected is random, the test begins with the illumination of the spots of the test grid with no predetermined order or rhythm, alternating between meridians and distances of approach to the center.

The time interval for the appearance of the test spots is variable and also programmed beforehand from the computer support. The patient is encouraged to press the button every time he can distinguish the presence of each of the light spots isolated from the central light focus.

Those non-discriminated light spots, which could be defined as hidden, border an area which is interpreted as occupied because of the luminous aberration and which serves as a basis for the calculation of the glare index (the index is obtained from the calculation of the percentage of the area covered by the halo, in relation to the test reference surface).

A fundamental condition for the performance of these determinations is the presence of scotopic environmental luminance that allows sufficient amplitude of night pupillary dilation. In previous studies, with all the lights in the room off and only the device on, suitable and stable environmental luminance was obtained. In these conditions, global illumination is below 0.17 lux.

We consider this method a direct method for the evaluation of these alterations or aberrations of scotopic vision. Application of this device and the method described reproduces in a laboratory the conditions of the prototype situation of night-time driving using an ad hoc light source of high intensity glare. In the measurements taken, the source luminance was calibrated at 458 $Cd/m^2$, which is representative of the density of light sources that these visual aberrations usually produce. Other previously developed computerized devices use high-resolution monitors, but even these cannot provide such levels of luminance.

DESCRIPTION OF A PREFERRED EMBODIMENT

Figure 1:
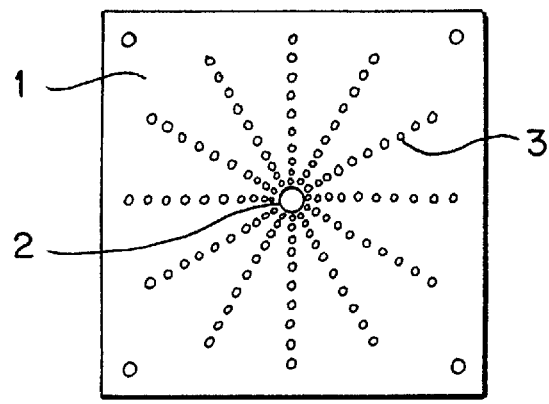
FIG. 1.
1.—Front screen. Central light source.
2.—Central light source.
3.—Light spots grid.
Figure 2:
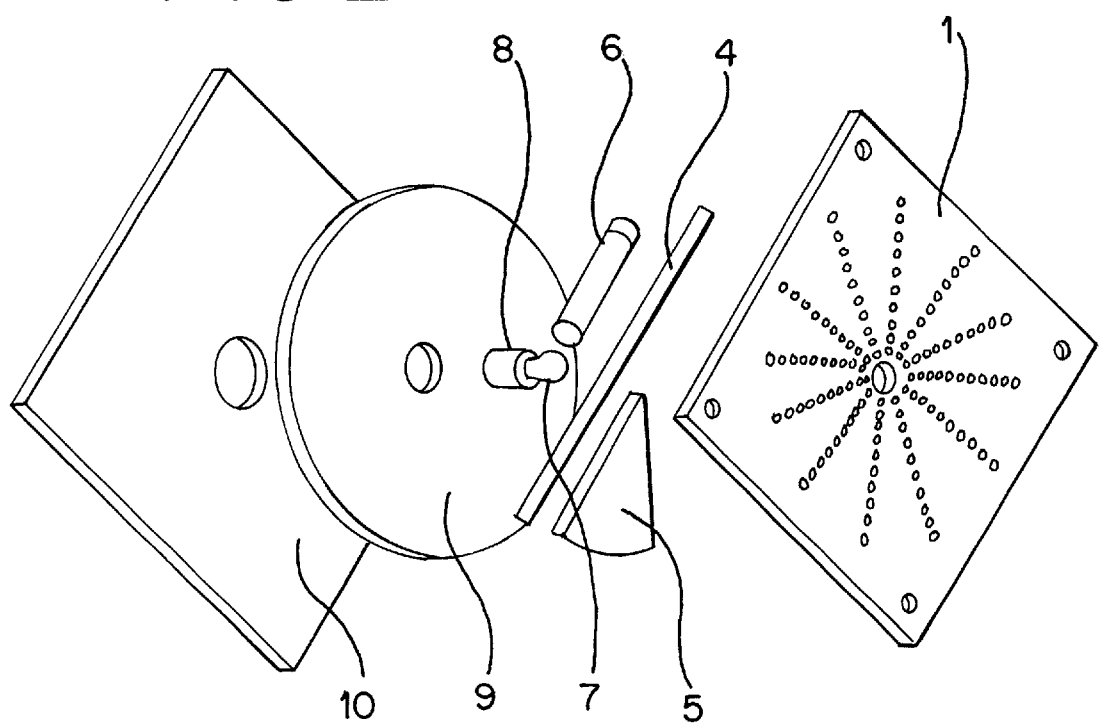
FIG. 2.
1.—Front screen.
4.—Cam.
5.—Interconnection plate between elements situated in the lever and brushes.
6.—Motor element.
7.—Central bulb.
8.—Bearing.
9.—Brush plate.
10.—Base of the box.

The internal means of carrying out the process is based on the displacement of a lever (4) whose interior houses a direct current motor (6) with a divider and which is controlled by a 4-quadrant chopper. This cam has 10 bulbs that illuminate the different spots of the same sector.

The positioning of the cam on the sectors is detected using sensors that stop the circular displacement and trigger the bulb sequence.

Bulbs and sensors are found on the lever (the bulbs are situated one in each hole aligned inside and the sensor, which is the schedule, is placed at the end in the rectangular window), the zero sensor will go above piece no. 10.

Piece no. 9, in the form of a disc, has different copper rings around which the brushes circulate to connect the cam elements with the exterior.

What is claimed is:

1. A device for the measurement of image degradation in scotopic vision, comprising:
   a) a screen with a dark background;
   b) a light on the screen;
   c) a means for centering the light on the screen;
   d) a means for adjusting the intensity of the light;
   e) a grid of at least four circles formed by light spots concentrically arranged around the central light on the screen.

2. The device of claim 1, wherein each circle on the grid is composed of 12 light spots equidistantly spaced.

3. The device of claim 1, wherein the grid of circular light spots is spaced according to the following manner: the concentric circle of spots closest to the central light source is about 4 mm from the central light source; the radii of the second, third, and fourth concentric circles are about 5 mm greater than the radii of the next innermost concentric circles; and the radii of the fifth to the tenth concentric circles are about 10 mm greater than the radii of the next innermost concentric circle.

4. The device of claim 1, wherein the light for the central light source and each of the light spots is supplied by fiber optic terminals.

5. The device of claim 4, wherein the intensity and illumination of each light is controlled by computer software.

6. The device of claim 1, additionally comprising a means to transfer orders for illumination of the spots.

7. The device of claim 6, wherein the means is a rotating cam system.

8. The device of claim 1, additionally comprising a connection which allows data collection by a computer.

9. The device of claim 8, additionally comprising a remote control trigger to activate data collection.

10. A method of measuring image degradation in scotopic vision in a patient, comprising the steps of:
    providing a screen with a dark background;
    providing a light on the screen;
    centering the light on the screen;
    adjusting the intensity of the light;
    providing a grid of at least four circles formed by light spots concentrically arranged around the central light on the screen;
    calibrating the intensity of the light spots;
    positioning a patient about two meters from the screen;
    directing the patient to fix one eye on the central light source; and
    covering the other eye of the patient.

11. A method in accordance with claim 10 and further comprising the step of sequentially illuminating the light spots in a pattern from the innermost concentric circle to the outermost concentric circle.

12. A method in accordance with claim 10 and further comprising the step of illuminating the light spots in a random pattern.

13. A method in accordance with claim 10 and further comprising the step of illuminating the light spots in a pattern selected by a user.

14. A method in accordance with claim 10 and further comprising the step of positioning 12 light spots equidistantly spaced to compose each circle.

15. A method in accordance with claim 10 and further comprising the following steps:
   positioning the concentric circle of spots which is closest to the central light source about 4 mm from the central light source;
   positioning the second, third, and fourth concentric circles so that the radius of each circle is about 5 mm greater than the radius of the next innermost concentric circle; and
   positioning the fifth through the tenth concentric circles so that the radius of each circle is about 10 mm greater than the radius of the next innermost concentric circle.

16. A method in accordance with claim 10 and further comprising the step of supplying light for the central light source and each of the light spots by fiber optic terminals.

17. A method in accordance with claim 16 and further comprising the step of controlling the intensity and illumination of each light by computer software.

18. A method in accordance with claim 10 and further comprising the step of transferring orders for illumination of the spots by means of a rotating cam system.

19. A method in accordance with claim 10 and further comprising the step of providing a connection which allows data collection by a computer.

20. A method in accordance with claim 10 and further comprising the step of providing a remote control trigger to activate data collection.

21. A method in accordance with claim 19 and further comprising the step of using the collected data to calculate a glare index.

22. method in accordance with claim 21 and further comprising the step of printing the collected data.

* * * * *

UNITED STATES PATENT AND TRADEMARK OFFICE
CERTIFICATE OF CORRECTION

PATENT NO. : 6,585,377 B2
DATED : July 1, 2003
INVENTOR(S) : Angel R. G. Ortega et al.

It is certified that error appears in the above-identified patent and that said Letters Patent is hereby corrected as shown below:

Title page,
Item [56], References Cited, insert the following:
-- FOREIGN PATENT DOCUMENTS
P200001523    6/2000    Spain --.

Signed and Sealed this

Twenty-fifth Day of January, 2005

JON W. DUDAS
*Director of the United States Patent and Trademark Office*